(12) United States Patent
Lee

(10) Patent No.: US 8,800,348 B2
(45) Date of Patent: Aug. 12, 2014

(54) PORTABLE MULTIFUNCTION CARDIAC SIMULATOR AND HEART VALVE TESTER

(75) Inventor: Shouyan Lee, Rancho Santa Margarita, CA (US)

(73) Assignee: Medical Implant Testing Lab, Inc., Irvine, CA (US)

( * ) Notice: Subject to any disclaimer, the term of this patent is extended or adjusted under 35 U.S.C. 154(b) by 228 days.

(21) Appl. No.: 13/160,387

(22) Filed: Jun. 14, 2011

(65) Prior Publication Data

US 2011/0303026 A1    Dec. 15, 2011

Related U.S. Application Data

(60) Provisional application No. 61/354,672, filed on Jun. 14, 2010.

(51) Int. Cl.
*G01L 27/00* (2006.01)
*A61F 2/24* (2006.01)

(52) U.S. Cl.
CPC .................................. *A61F 2/2472* (2013.01)
USPC ........................................................ 73/1.72

(58) Field of Classification Search
None
See application file for complete search history.

(56) References Cited

U.S. PATENT DOCUMENTS

| | | | | |
|---|---|---|---|---|
| 4,078,267 A | * | 3/1978 | Cieszynski | 623/3.12 |
| 4,381,663 A | * | 5/1983 | Swanson | 73/37 |
| 4,450,710 A | * | 5/1984 | Nettekoven | 73/37 |
| 4,546,642 A | * | 10/1985 | Swanson | 73/37 |
| 4,682,491 A | * | 7/1987 | Pickard | 73/37 |
| 5,272,909 A | * | 12/1993 | Nguyen et al. | 73/37 |
| 5,531,094 A | * | 7/1996 | More et al. | 73/1.72 |
| 2010/0154507 A1 | * | 6/2010 | Matonick | 73/1.72 |
| 2011/0132073 A1 | * | 6/2011 | McCloskey et al. | 73/37 |

* cited by examiner

*Primary Examiner* — Robert R Raevis
(74) *Attorney, Agent, or Firm* — WPAT, P.C.; Anthony King

(57) ABSTRACT

A testing system for testing a prosthetic valve. The system includes a housing having a main channel defines a circuitous flow path for a fluid. The solid housing also includes a chamber which in turn includes a piston having an opening at the bottom end. The piston moves in a reciprocating motion within the chamber. Further, a holding mechanism, for holding a prosthetic valve, is positioned within the main channel at either or both sides of the chamber, or within the opening in the piston. A user of the device may selectively control a flow path of the fluid between 1). having the fluid flow through the prosthetic valve installed in the piston, and 2). having no fluid passing though the piston.

18 Claims, 7 Drawing Sheets

PORTABLE MULTIFUNCTION CARDIAC SIMULATOR AND HEART VALVE TESTER

CROSS-REFERENCE TO RELATED APPLICATIONS

This application claims priority to, U.S. Provisional Pat. No. 61/354,672, filed on Jun. 14, 2010, hereby incorporated by reference in its entirety.

FIELD OF THE INVENTION

The present disclosure relates generally to prosthetic valve simulators and testers, and more particularly to a portable multifunction tester and simulator for prosthetic heart valves.

BACKGROUND

The advent of the prosthetic heart valve has provided many patients with both improved quality of life and increased longevity. The primary function of a prosthetic heart valve is to act as a check valve, opening to permit antegrade blood flow and closing to prevent retrograde flow, about one hundred thousand times a day. The valve elements move in response to a threshold pressure gradient in one direction, allowing flow through the valves, while closing in the opposite direction, preventing reverse flow below the threshold pressure gradient.

Prosthetic heart valves go through extensive testing and quality checks because failure of the valves in vivo can have catastrophic results. Certain characteristics such as durability, and proper fluid flow, are rigorously tested before a valve is deemed fit.

Currently, valve testing may be accomplished by two known techniques—pulse duplicator testing and accelerated wear testing. The systems facilitating these tests are typically large in size owing to numerous connection tubing and pipes.

Therefore, there is an apparent need for a simple and compact system that facilitates pulse duplicator testing and accelerated wear testing techniques, without any performance drawbacks.

SUMMARY OF THE INVENTION

Embodiments of the present disclosure are directed to a testing system. One such embodiment describes a prosthetic valve testing system including a solid housing having a main channel defining a circuitous flow pattern for a fluid. The main channel includes a bifurcation that defines a first flow path and a second flow path. The solid housing also includes a chamber, in flow communication with the main channel, including a piston having an opening at the bottom end. The piston moves in a reciprocating motion within the chamber. Further, a holding mechanism, for holding a prosthetic valve, is positioned within the main channel at either or both sides of the chamber, or within the opening in the piston.

Another embodiment of the present disclosure describes a prosthetic heart valve testing system. The system includes a housing and a main channel, and within the housing, defining a circuitous flow pattern for a fluid. The main channel defines a first flow path. A chamber, in flow communication with the main channel, includes a piston moving in a reciprocating motion. Further, one or more holding mechanisms, coupled to the main channel, hold the prosthetic valve. The holding mechanisms are positioned such that the prosthetic valves can be positioned at either or both sides of the chamber or within the chamber.

These and other aspects, and features of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment. The drawings are illustrative in nature and are not necessarily drawn to scale.

DETAILED DESCRIPTION

Figure 1:
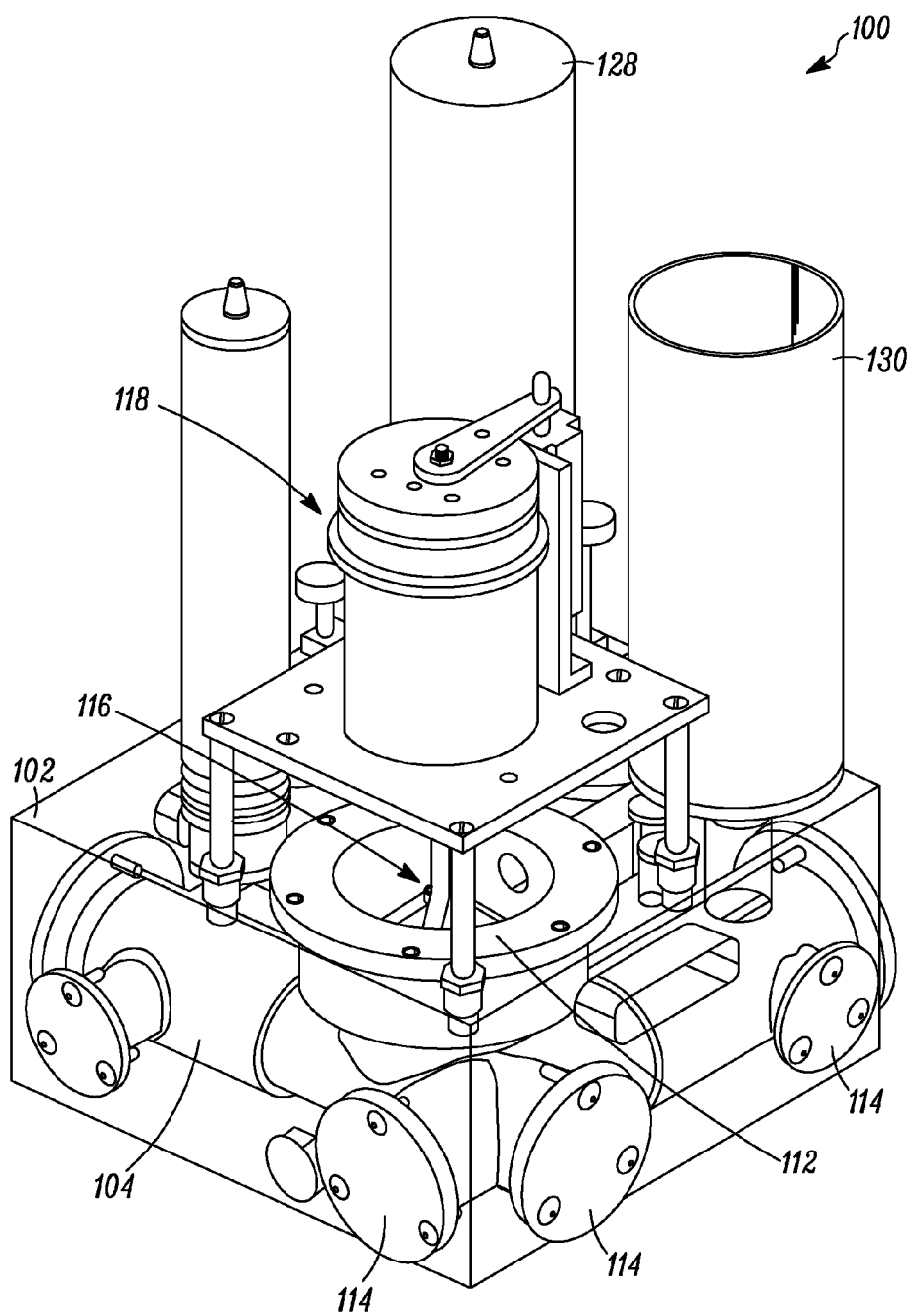
FIG. 1 illustrates a perspective view of a prosthetic valve testing system according to embodiments of the present disclosure.

To promote an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments and any further applications of the principles of the disclosure as illustrated therein are contemplated as would normally occur to one skilled in the art to which the disclosure relates. All limitations of scope should be determined in accordance with and as expressed in the claims.

OVERVIEW

Embodiments of the present disclosure describe a compact system for testing prosthetic valves. The system allows pulse duplicator testing and accelerated wear testing of the prosthetic valve by defining two fluid flow paths within a single solid block. Two flow paths are defined by dividing a main channel, within the solid block, into two channels—a simulation channel (for pulse durability testing) and a durability channel (for accelerated wear testing)—at a bifurcation point. The system also includes a chamber, in fluid communication with the main channel, having a piston that moves in a vertical reciprocating motion.

The first flow path is defined by blocking the durability channel and by blocking fluid flow across the chamber. The prosthetic valves are positioned within the main channel at both the inlet and outlet ends of the chamber. The fluid circulates within the main channel through the simulation channel via the two prosthetic valves.

The second flow path is outlined by blocking the simulation channel and positioning a prosthetic valve within an opening in the piston. The fluid circulates within the main channel through the durability channel and the chamber via the opening in the piston, which holds the valve.

In each of the scenarios, the vertical reciprocating motion of the piston simulates a heart's pumping function. As piston reciprocates, the fluid flows through the main channel and one of the simulation or durability channel, which holds the prosthetic valve. A heating rod positioned within the system may increase the temperature of the fluid, as desired. For proof testing, the system employs a set of sensors to monitor the prosthetic valves. Further, the solid block is transparent to observe the valves conveniently. Thus, the two testing techniques employed by the present disclosure can be used to verify the efficacy of prosthetic valves and to improve their design by identifying areas of leakage or migration.

EXEMPLARY EMBODIMENTS

Figure 2:
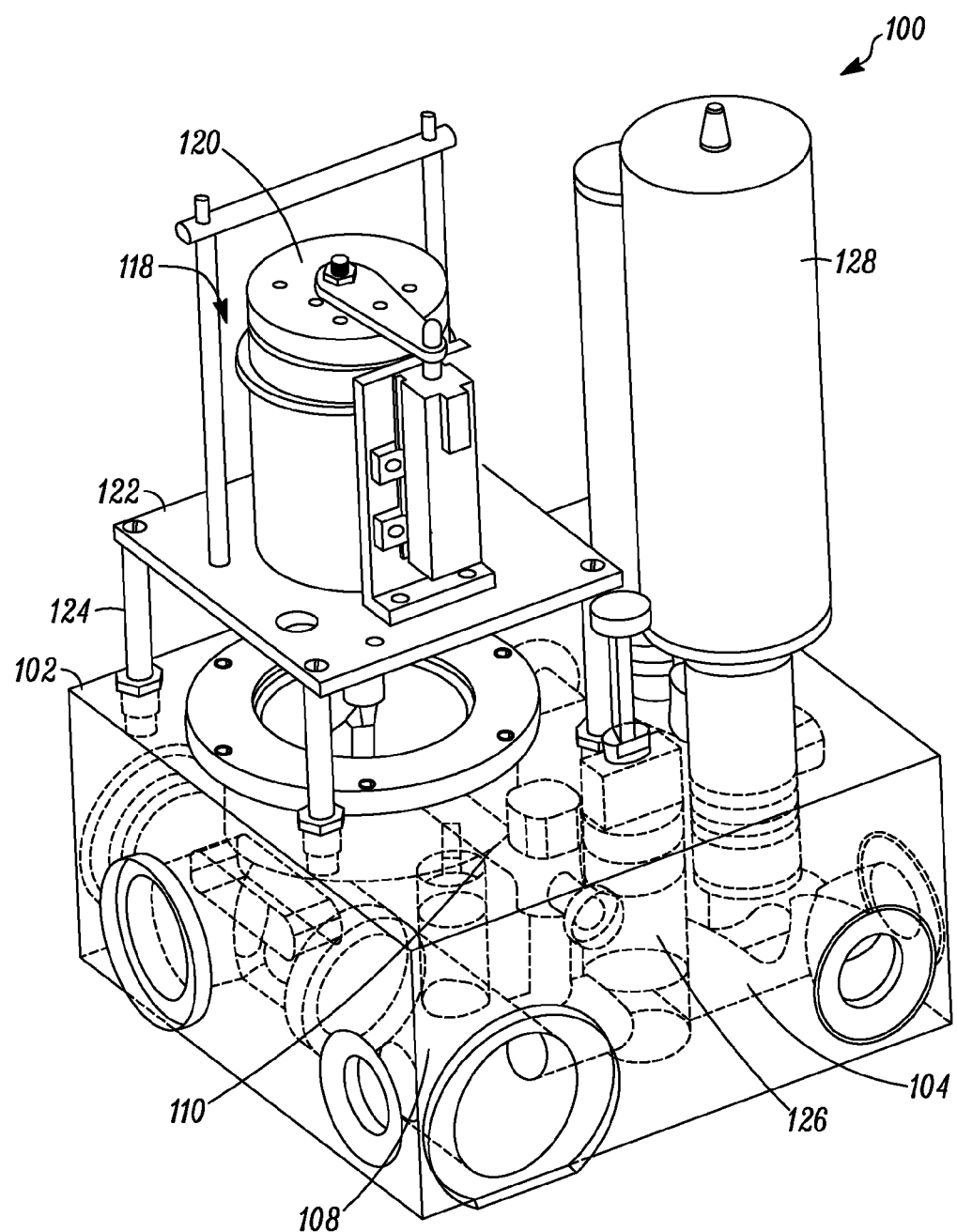
FIG. 2 illustrates a perspective views from an opposite side of FIG. 1, of the same prosthetic valve testing system where the reservoir is removed and plugged-up, according to embodiments of the present disclosure. The side ports are shown to be open, without any covering plates.

FIGS. 1 and 2 illustrate an exemplary testing system 100 that tests a prosthetic valve such as a prosthetic heart valve. The system 100 includes a housing 102 having a main channel 104, which bifurcates at a point 106 to define two channels—a simulation channel 108 and a durability channel 110. The system 100 also includes a chamber 112 in fluid communication with the main channel 104. One or more prosthetic valves (not shown) may be mounted within the system for proof testing.

The housing 102 is a solid transparent block made of acrylic, polycarbonate, or other suitable material. The housing 102 is transparent for easy observation of the prosthetic valve during testing. A main channel 104 is drilled into the housing and subsequently, the openings on the outer surface are covered using cover plates 114. Once the openings are covered, the main channel 104 provides a closed loop path for fluid flow within the housing 102. It should be understood that any desired flow channel design may be drilled into this solid housing 102.

Although the disclosed embodiment is manufactured by drilling four straight channels (that intersects with each other) into a solid transparent block of acrylic material, one skilled in the art would appreciate other suitable synthetic or natural polymeric material can also be used. One skilled in the art would also appreciate the channels can be created by other means known in the manufacturing art. For example, one may create the housing 102 (having internal channels) by injection molding, or by 3-D printing. Further, the housing does not have to be a solid piece of material. For example, the channel 104 can be transparent pipes and tubing installed inside of a transparent hollow housing.

Figure 5:
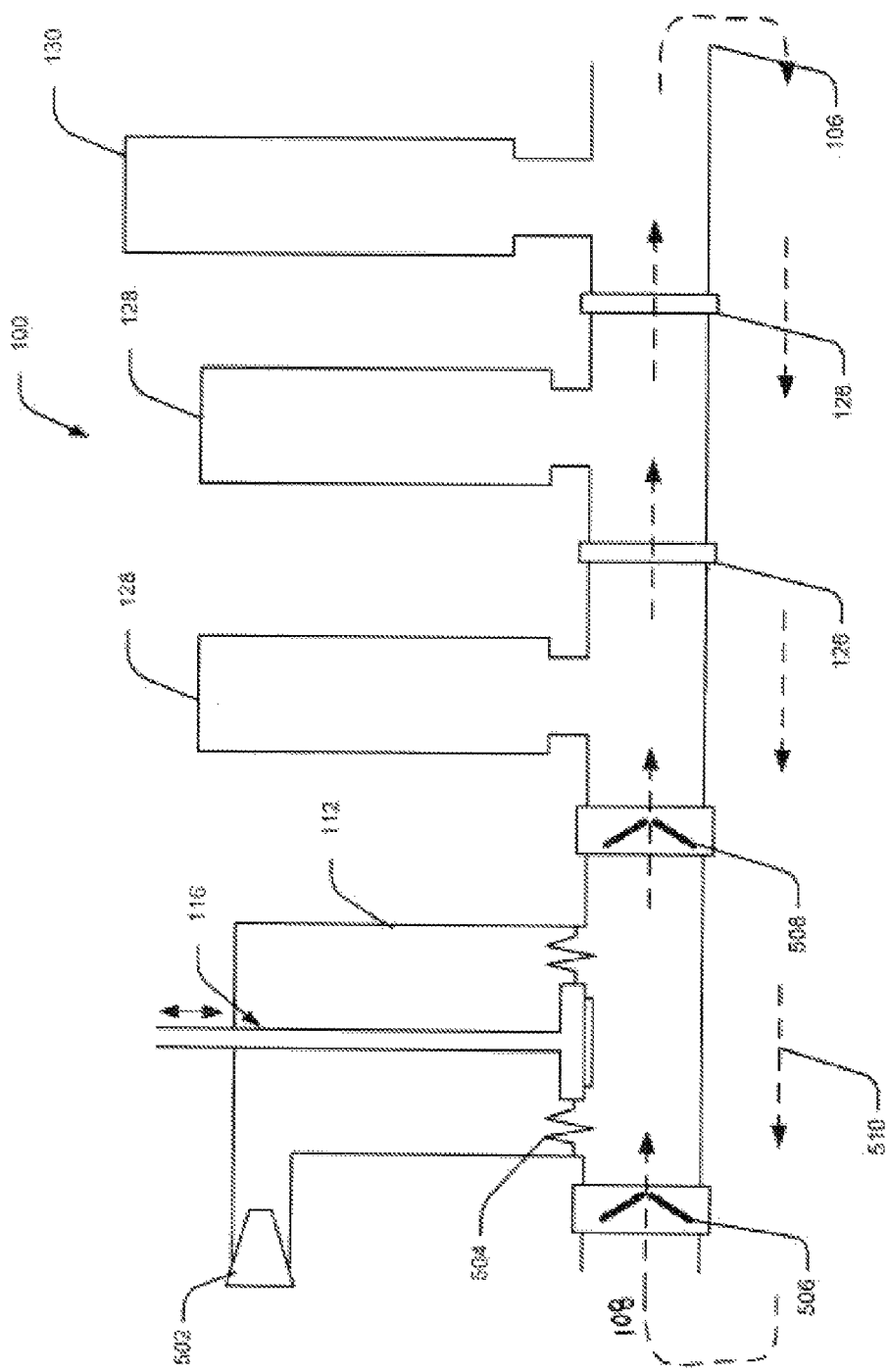
FIG. 5 illustrates a flow path for implementing pulse duplicator testing using the system shown in FIG. 1.

The main channel 104 is generally a cylindrical hollow passage that forms a circuitous flow pattern for any fluid. At the bifurcation point 106, the main channel 104 divides into the simulation channel 108 and the durability channel 110. Each of these sub-channels leads back to the main channel 104 to define a complete flow path. At any point, the fluid flows through either the simulation channel 108 (as shown in FIG. 5) or the durability channel 110 (as shown in FIG. 7). Channels 108 and 110 allow the system to perform pulse duplicator testing and accelerated wear testing, respectively. Each of these channels along with their test functionalities will be discussed in the following sections in connection with FIGS. 5-7.

The chamber 112 is also drilled into the housing 102. But as previously mentioned, one skilled in the manufacturing art would immediately appreciate other suitable ways to create chamber 112. As shown, the chamber 112 is typically a cylindrical-shaped housing for mounting a piston assembly 116. The piston assembly 116 is mounted vertically within the center of the chamber 112, creating a uniform gap between the piston assembly 116 and the inner chamber wall. To seal this gap, the system 100 employs a diaphragm (504 of FIG. 7), such as a rolling diaphragm, constructed of a non-reactive and flexible thin rubber, polymeric or synthetic based material. The flexible diaphragm 504 is highly compliant, with low resistance to axial deformation across its entire axial range of motion within the chamber 112. Thus, the diaphragm exerts very little resistance to piston movement, and prevents any fluid from passing through.

Figure 3:
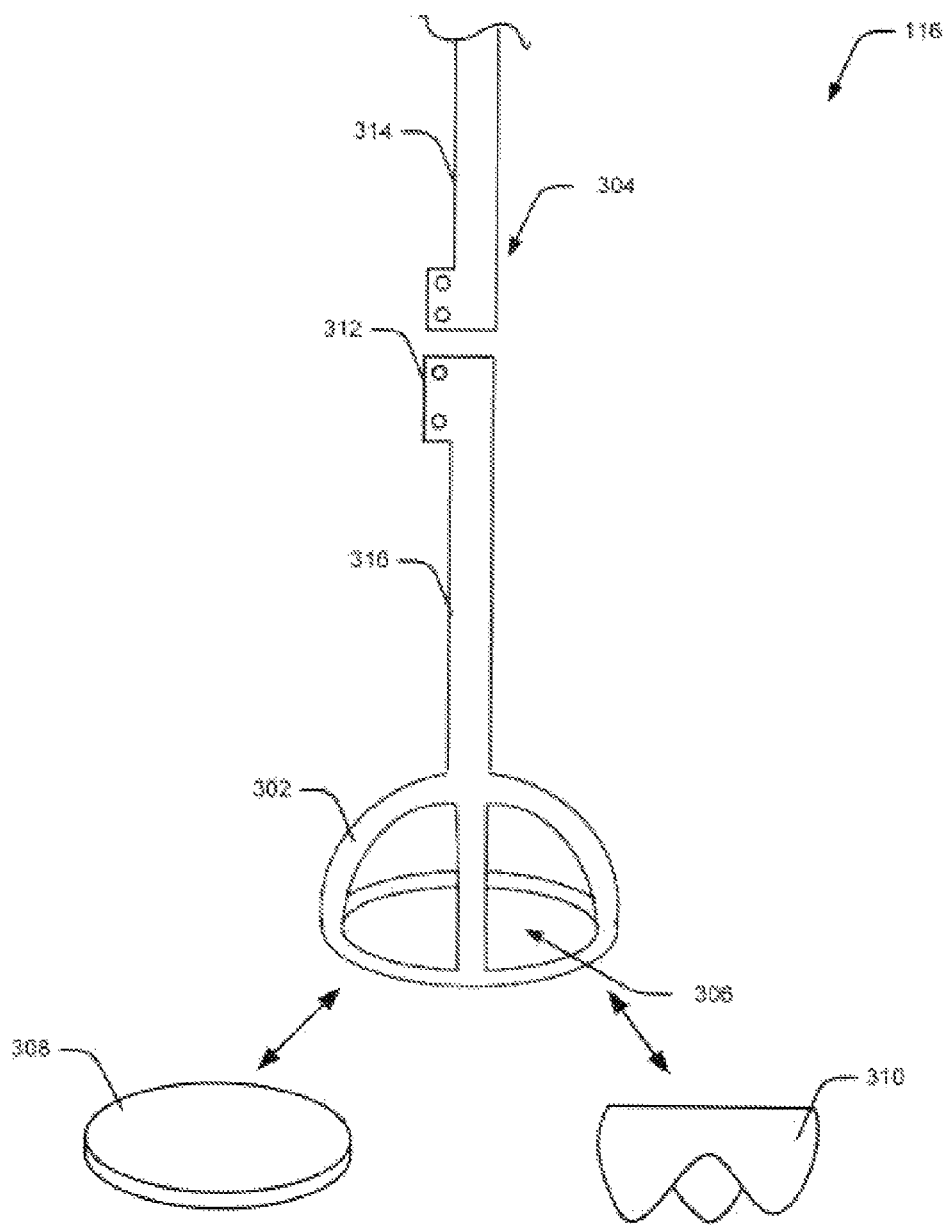
FIG. 3 illustrates a piston assembly according to an embodiment of the present disclosure.

The piston assembly 116 is adapted to move in a reciprocating vertical motion within the chamber. FIG. 3 illustrates an exemplary piston assembly, such as the piston assembly 116. As shown, the piston assembly 116 includes a piston 302 having its top end connected to a shaft 304. The piston 302 includes an opening 306, which is a through-hole at the bottom surface. In an embodiment, this opening 306 may be covered by a stopper 308 (a cover plate, or other suitable structure to close the through-hole) or may house a prosthetic valve 310. The stopper 308 is a solid disc-shaped structure that is detachably connected to the opening 306, preventing fluid flow through the piston 302. Although FIG. 3 does not specifically show how the stopper 308 and the valve 310 is attached to the piston 302, such mechanism is well known in the art and does not require further explanation here. The key is to have them securely attached to the piston 302 so that the stopper, when installed, can stop flow of fluid, and effectively pump the fluid in the chamber as shown in FIG. 5. And when a valve is installed in the piston 302, the valve allows fluid flow therethrough for durability testing as typically done.

Further, the vertical shaft 304 may include a detachment section 312 to divide the vertical shaft 304 into two sections 314 and 316. This detachable section allows easy removal of the piston assembly 116 from the housing 102. Those skilled in the art will appreciate that any known piston structure that can exhibit reciprocating motion within the chamber 112 may replace the piston 302.

Referring back to FIG. 1, a driver motor assembly 118 enables axial displacement of the piston assembly 116. The driver motor assembly 118, connected to the top end of the piston assembly 116, includes a drive motor 120 mounted on a supporting plate 122, which in turn stands on the solid housing 102 using one or more supporting members 124. As shown, the supporting members 124 are solid bars, made of metal or a suitable material, fixed onto the top surface of the housing 102 using known detachable mechanisms such as span fit or screws. This detachable mechanism allows the drive motor assembly 118 to easily mount on or separate from the housing 102, as desired. Further, a controller (not shown) may control the driving force provided by the drive motor 120 and provide a control signal to the motor 120 to induce a corresponding piston motion.

The piston assembly 116 enables circuitous flow of fluid within the system 100. As discussed in FIG. 3, the piston assembly 116 includes the piston 302, mounted within the chamber 112, and the shaft 304 that extends out from the chamber 112. The top end of the shaft 304 connects to the drive motor assembly 118. As the motor 120 drives the shaft 304 up and down, the piston 302 experiences axial reciprocating motion within the chamber 112. This axial reciprocating motion provides a motive force to drive the testing fluid through cycles within the main channel 104. The reciprocally moveable piston assembly 116 pressurizes and depressurizes the fluid underneath it.

In an embodiment of the present disclosure, the chamber 112 along with the reciprocating piston 302 simulates the pumping function of a heart. The fluid in turn circulates within the main channel 104 that acts as a circulatory system. In such embodiments, the control signal provided by the controller may be a pulse width modulated signal or any desired signal that simulated different heart conditions such as tachycardia or bradycardia. The prosthetic valves to be tested are positioned at desired locations within the fluid flow path.

The prosthetic valves, such as the valve 310, simulate the function of a natural valve. In an embodiment, the prosthetic valves can be designed as replacements for any heart valves, i.e., aortic valves, mitral valves, tricuspid valves, or pulmonary valves. In addition, valved prostheses can be used for the replacement of vascular valves. Moreover, the prosthetic valves may be implanted in an animal or a human body. These valves are mounted on holding mechanisms (see FIG. 4) within the system 100. The following section describes one such holding mechanism.

Figure 4:
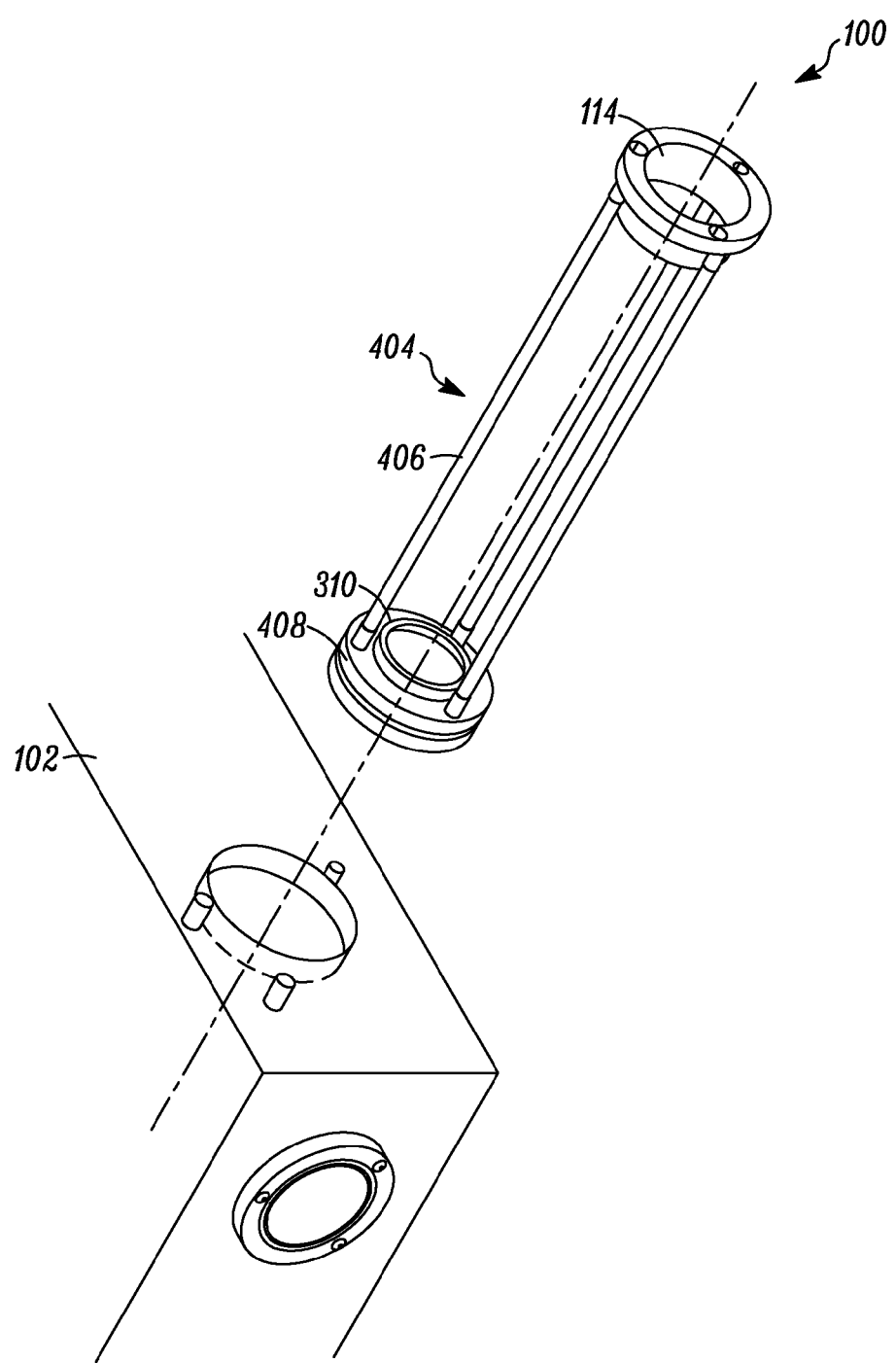
FIG. 4 illustrates an exemplary holding mechanism for positioning a valve within the system shown in FIG. 1.

FIG. 4 illustrates an exemplary holding mechanism 400 for introducing an exemplary valve, such as the valve 310 within the system 100. The illustrated embodiment depicts the transparent cover plate 114 attached to a scaffold structure 404 that can hold the valve 310. As shown, the cover plate 114 is a generally circular plate substantially covering the drilled side openings on the housing 102. These cover plates 114 are transparent plates and replaceable plates that can be pulled out of the system 100, as desired. The inner surface of the cover plate 114 is attached to the scaffold structure 404, which includes multiple solid rods 406 extending from the inner surface in a perpendicular direction. The other ends of the rods 406 are connected to a ring shaped structure 408 that can hold any desired prosthetic valve such as the valve 310.

To position the valve 310, the cover plate 114 may be retrieved (by unscrewing three fastening screws. Screws are not shown in FIG. 4 but the screw holes are) and the valve 310 may be placed within the ring-shaped structure 408. Subsequently, the cover plate 114 may be positioned in the housing opening. The cover plate 114 may be fixed onto the housing known detachable means such as span fit attachment or screws. The length of the rods 406 may be adjusted to position the valve 310 at a desired location (see 506 and 508 in FIGS. 5 and 6) within the main channel 104. Further, the inner diameter of the ring-shaped structure 408 may also be customized based on the shape and size of the valve 310 to be tested.

Once the valve 310 is positioned, testing fluid flows through the system 100. In general, the testing fluid is a liquid that is approximately incompressible over the fluid pressures experienced in the testing system 100. Generally, any liquid can be used that does not react with or otherwise deteriorate the valve or the system 100. Examples of the testing fluid include water, saline solutions, organic solvents, or other aqueous liquids.

Referring back to FIGS. 1 and 2, the system 100 also includes other known components during testing. Among other devices, the system 100 includes a flow resistant module 126, a compliance module 128, and a fluid reservoir 130. The flow resistance modules 126 are flow obstruction adding along the flow path at desired locations within the channel 104. As shown, the compliance module 128 and the fluid reservoir 130 are tall cylindrical shaped structures mounted vertically on the housing 102 using detachable means. The reservoir 130, as the name suggests, supplies fluid to the system, and may include an open top to refill the fluid. The open top may be covered with a replaceable lid. These devices are known in the art and will not be discussed in detail. Moreover, a set of sensors, such as pressure and temperature sensors, may also be mounted onto the system 100 for proof testing a prosthetic valve, such as the valve 310. In addition, heating mechanism may be incorporated to check the operability of the valves at high temperatures. These sensors and heating rod can be installed via any of the cover plates 114, much similar to how the scaffold is inserted through the side opening by first uncovering the cover plate 114 as shown in FIG. 4.

The present disclosure provides two major functionalities—pulse duplicator testing and accelerated wear testing of a valve. To this end, the main channel 104 is divided into the simulation channel 108 and the durability channel 110. Each channel describes a different flow path for the fluid. The following section describes the flow path for each testing technique in connection with FIGS. 5-7.

The channels 108 and 110 are referred to as "simulation channel" and "durability channel" for description purposes. It should be apparent to those skilled in the art that these channels are typical hollow cylindrical passages formed in the housing 102 to allow fluid flow. The cross sectional shape of the channels may be circular, square, rhombus, or any irregular shape, as desired.

FIG. 5 illustrates a cross-section view of the system 100 depicting the flow path described by a fluid during pulse duplicator testing. As shown, the fluid traverses through the simulation channel 108. During this testing, the bottom opening 306 on the piston 302 is sealed by the stopper 308 to block fluid flow through the durability channel 110 and across the chamber 112. In an implementation, the durability channel 110 is also blocked using a plug 502. It should be noted that plug 502 is shown in this simplified diagram as a typical bottle stopper. In actual embodiments, any other flow-blocking mechanism, e.g., gate, valve, can be used such that a user may selectively open or close the durability channel.

Further, a diaphragm 504 seals the gap between the piston 302 and chamber walls to prevent fluid flow through the chamber 112. Two valves 506 and 508 are positioned within the main channel 104 such that the valves lie on either side of the chamber 112. In an embodiment, only a single valve may be placed at either end of the chamber 112.

The flow path is defined by the fluid passing through the main channel 104, via the valves 506 and 508, in a direction shown by an arrow 510. The fluid traverses in only the illustrated direction. As shown, the fluid flows through the main channel 104 via the valve 508 and the resistance modules 126. At the bifurcation point 106, the fluid is routed through the simulation channel 108 to contact the valve 506. The fluid flows continuously through this closed flow path loop.

The simulation testing is accomplished by the operation of the piston assembly 116. The piston 302 moves in a vertical reciprocating manner within the chamber 112, simulating the heart's pumping function. The valves 506 and 508, disposed at the inflow and outflow ends of the chamber 112, experience difference in flow pressure. In an implementation, the valves 506 and 508 may be mitral valves and aortic valve. When the piston goes up, the valve 506 opens to allow the fluid to enter the region under the piston assembly 116 and subsequently, as the piston assembly 116 goes down, the valve 508 opens to allow the fluid to traverse along the main channel 104 in the direction depicted by the arrow 510. At this point, the valve 506 closes to block reverse flow of the fluid. Further, when the piston assembly 116 goes up the valve 508 closes to prevent back flow of fluid in a direction opposite to the arrow 510. The transparent housing 102 allows convenient visual monitoring of the valves during this process. A user may visually look through the transparent housing 102 and/or through any of the transparent cover plates 114 to see valves 506 and 508 in operation.

Further, the controller (e.g., electronic gauges, microprocessor, computer systems, computer programs) monitors fluid pressure, fluid temperature, and other perimeters during testing of valves 506 and 508 within the system 100. The controller may also manipulate the axial movement of the piston assembly 116 to test the operation of the valves 506, 508 at different simulated heart conditions. In addition, other system components are also employed that assist in proof testing the valves 506 and 508.

Figure 6:
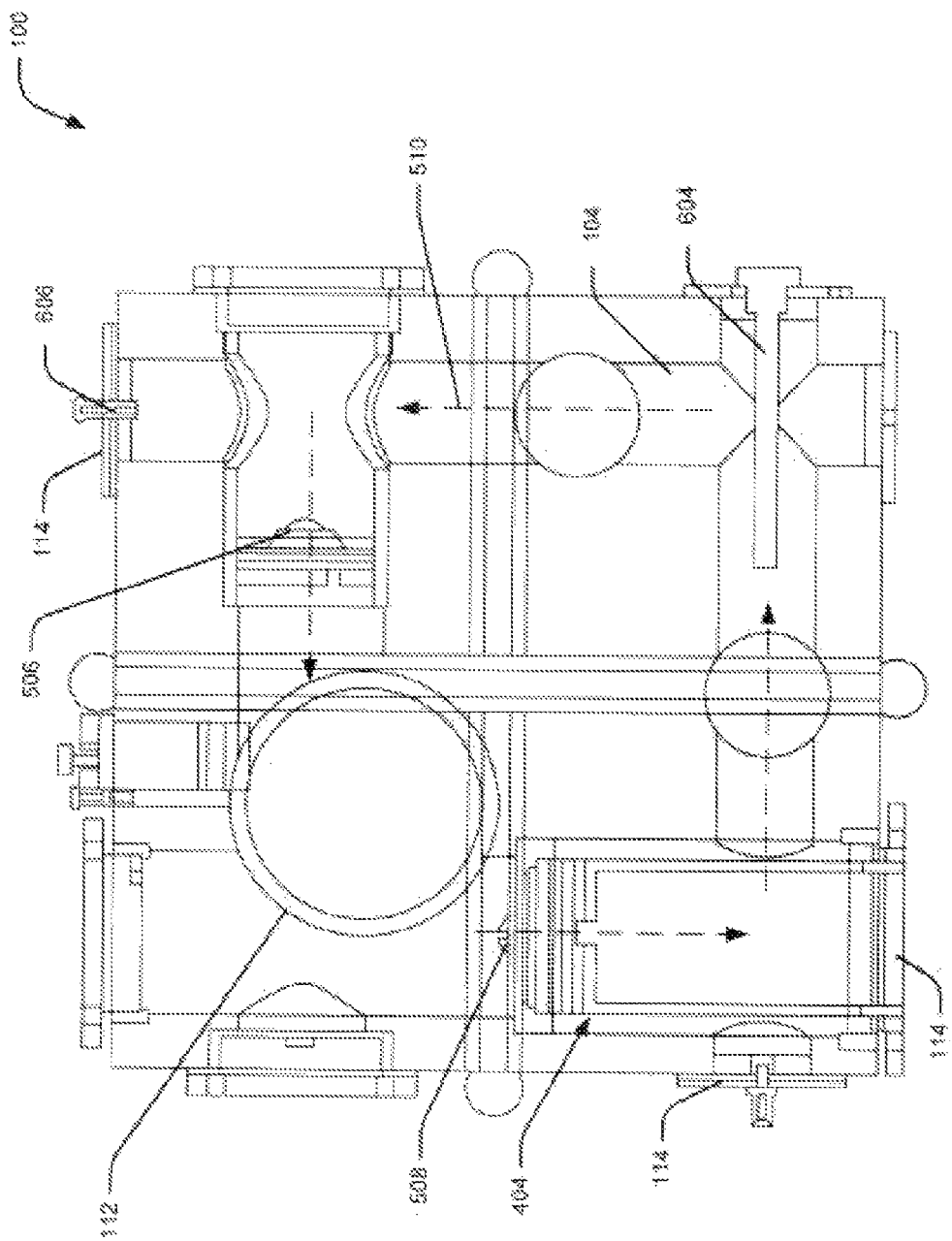
FIG. 6 illustrates a top view of the system, shown in FIG. 1, during pulse duplicator testing.
Figure 7:
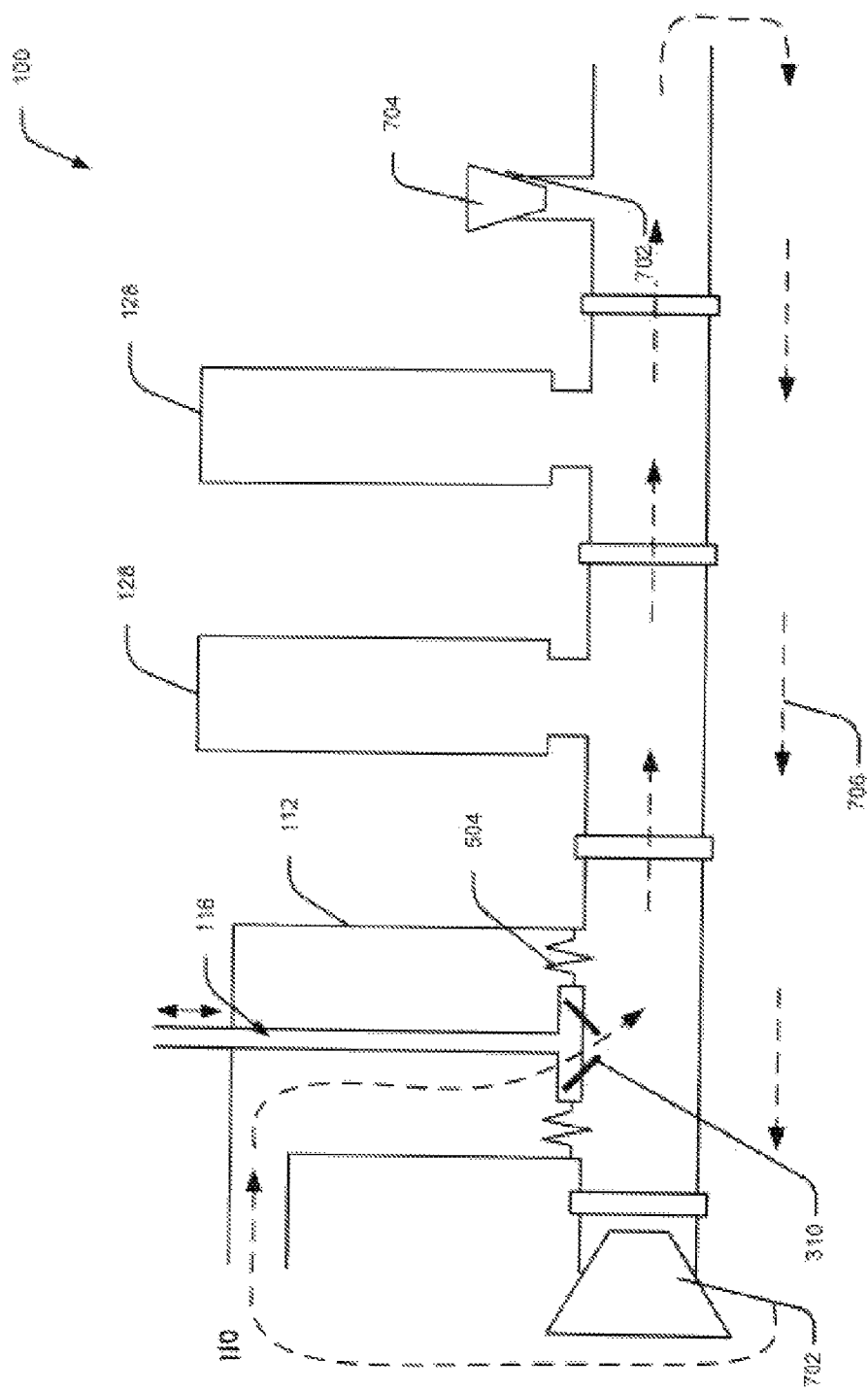
FIG. 7 illustrates a flow path for implementing accelerated wear testing using the system, shown in FIG. 1.

FIG. 6 depicts a top view of the system 100 showing flow path for pulse duplicator testing along with the additional testing components. The valves 506 and 508 are positioned on a holding mechanism such as the scaffold 404 connected to the cover plate 114. As shown, these valves are placed within the main channel 104, at either end of the chamber 112. A heating rod 604 is inserted through the cover plate 114 to increase the temperature of the fluid. In addition, the cover plate 114 may house testing components such as sensors 606, which may be pressure sensor and/or temperature sensor. The control module may monitor these sensors and heating elements to verify the conditions of the test environment and compatibility of the valves 506, 508 to the circulatory system.

FIG. 7 illustrates another sectional view of the system 100 depicting the flow path described by a fluid during accelerated wear testing. To switch the system 100 from pulse duplicator testing mode to accelerated testing mode, the simulation channel 108 is blocked using a plug 702 (plug 702 is a simplified illustration of mechanisms such as flow gate and flow valve, where a user may open or close the flow path from a control knob on the outside of the housing 102), the fluid reservoir 130 is removed, and a plug 704 is placed in its position. Instead of plugs, any know blocking device or mechanism may be used to block the channel 108 and the fluid reservoir hole. A valve, such as the valve 310, is positioned within the piston opening 306. The valve 310 may be directly positioned along the edges of the opening or an additional holding mechanism such as the ring shaped structure 408, shown in FIG. 3, may be employed to deploy the valve 310. It should be understood that any known holding mechanism that can position a prosthetic valve within the system 100 may be employed.

To deploy the valve 310, the drive motor assembly 118 can be retrieved by removing the rods 124 attached onto the housing 102. As already discussed, the rods 124 may be attached using a locking nut mechanism that can be loosened to remove the drive motor assembly 118 from the system 100. The shaft 304 is separated along with the drive motor assembly 118. To avoid damage to the piston assembly and the diaphragm 504, in an implementation, the securing mechanism attaching the two sections of the shaft 304 are first detached such the only the section 314 of the shaft 304 is removed along with the drive motor assembly 118. Subsequently, with the drive motor 118 now out of the way, a user may reach into the chamber 112 and replace the stopper 308 with a valve 310.

Upon valve deployment, the fluid circulates within the durability channel 110 defining a flow path, depicted by an arrow 706. As shown, the fluid flows in the main channel 104 through the resistance modules 128 up to the bifurcation point 106. At this point, the fluid is directed towards the durability channel 110. Subsequently, the fluid enters the chamber 112 and passes through the piston opening 306 via the valve 310. The fluid again enters the main channel 102 and circulates through this flow path repeatedly. When the piston assembly 116 goes upwards, the valve 310 opens to allow the fluid to pass through. Subsequently, when the piston assembly 116 moves downwards, the valve 310 closes. During this process, the piston 302 continuously reciprocates in the axial direction allowing the fluid to flows through the valve 310.

It should be apparent that the fatigue testing for the prosthetic valve 310 is performed at an accelerated rate. The human heart generally beats at a frequency from about 50 to about 200 cycles/beats per minute. Accelerated wear testers for valves generally operate in the range of about 400 cycles per minute to about 1200 cycles per minute. Thus, the piston moves up and down at such a high frequency to check the durability of the prosthetic valve 310.

The present disclosure facilitates proof testing of a prosthetic valve by performing pulse duplicator testing and accelerates wear testing using a single block device. Each testing technique requires a different fluid flow path. The present disclosure enables selectively directing the fluid to one of the simulation channel or the durability channel to perform the pulse duplicator testing or the accelerated wear testing, respectively. In an implementation, a user or a technician may identify the desired flow path or the controller may automatically select the desired flow path.

The specification has set out a number of specific exemplary embodiments, but those skilled in the art will understand that variations in these embodiments will naturally occur in the course of embodying the subject matter of the disclosure in specific implementations and environments. It will further be understood that such variation and others as well, fall within the scope of the disclosure. Neither those possible variations nor the specific examples set above are set out to limit the scope of the disclosure. Rather, the scope of the present disclosure is defined solely by the claims set out below.

What is claimed is:

1. A testing system comprising:
 a body including;
   a main channel having a circuitous flow pattern for a fluid, defining a first flow path;
   a chamber connected to the main channel;
   a sub-channel that branches off the main channel, wherein a first end of the sub-channel is connected to the main channel and a second end of the sub-channel is fluidly connected to an upper side of the chamber, defining a second flow path;
 a user-actuatable gate disposed in either the main channel or the sub-channel to control an amount of fluid flow in the first flow path and in the second flow path;
 a piston mounted within the chamber, the piston having a reciprocating movement and including an opening at a bottom end of the piston; and
 at least one detachable holding mechanism to hold at least one prosthetic valve, the at least one detachable holding mechanism being positioned within the main channel at either side of the chamber, or within the opening in the piston.

2. The system of claim 1, wherein the body is made of a single solid block of transparent material.

3. The system of claim 1, wherein the fluid circulates through one of:
 the first flow path; or
 the second flow path.

4. The system of claim 3, wherein the opening in the piston is covered with a solid stopper, when the fluid passes through the first flow path.

5. The system of claim 3, wherein a first prosthetic valve is disposed on a first holding mechanism and a second prosthetic valve is disposed on a second holding mechanism, wherein the first holding mechanism and the second holding mechanism are positioned at either side of the chamber when the fluid passes through the first flow path.

6. The system of claim 3, wherein one of the at least one prosthetic valve is disposed on one of the at least one holding mechanism positioned within the opening in the piston when the fluid passes through the second flow path.

7. The system of claim 1 further comprising at least one of:
a flow resistance module fluidly coupled to main channel;
a compliance module fluidly coupled to main channel;
a fluid reservoir fluidly coupled to main channel;
a heating element removably inserted into the main channel; or
a sensor removably inserted into the main channel.

8. The system of claim 1, wherein the chamber includes a diaphragm disposed along the circumference of the piston such that the diaphragm seals the space between the piston and the chamber inner walls.

9. The system of claim 1 further comprising a motor connected to the piston to enable a reciprocating motion of the piston.

10. The system of claim 1 further comprising a controller electronically coupled to the system to monitor and adjust a testing parameter.

11. A system for testing prosthetic heart valves, the system comprising:
a housing;
a main channel disposed within the housing having a circuitous flow pattern for a fluid, defining a first flow path;
a chamber connected to the main channel;
a sub-channel that branches off the main channel, wherein a first end of the sub-channel is connected to the main channel and a second end of the sub-channel is fluidly connected to an upper side of the chamber, defining a second flow path;
a piston mounted within the chamber, the piston having a reciprocating movement; and
at least one detachable holding mechanism to hold at least one prosthetic heart valve, the at least one detachable holding mechanism being positioned such that the prosthetic heart valve can be positioned within the main channel at either side of the chamber, or at a through-hole in the piston.

12. The system of claim 11 further comprising a user-actuatable gate disposed in either the main channel or the sub-channel to control an amount of fluid flow in the first flow path or the second flow path.

13. The system of claim 11, wherein the housing is a transparent block of acrylic material.

14. The system of claim 11, wherein the at least one holding mechanism is detachably positioned through a side opening of the housing, wherein the at least one holding mechanism includes a scaffold and a back transparent plate through which visual monitoring of the prosthetic valve is possible when the prosthetic valve is positioned in the main channel.

15. The system of claim 11, wherein the through-hole in the piston is capable of interchangeably switching between the following two modes:
a) allowing the fluid to pass through, and one of the at least one detachable holding mechanism is positioned at the through-hole to hold one of the at least one prosthetic heart valve so that when the fluid passes through the through-hole, it also passes through the prosthetic heart valve; or b) wherein a stopper is detachably coupled to the through-hole in the piston, capable of completely blocking passage of the fluid through the through-hole when the detachable prosthetic heart valve is not positioned at the through-hole.

16. The system of claim 11 further comprising at least one member selected from a group consisting of:
a) a flow resistance module fluidly coupled to the main channel;
b) a compliance module fluidly coupled to the main channel;
c) a fluid reservoir fluidly coupled to the main channel;
d) a heating element removably inserted into the main channel; and
e) a sensor removably inserted into the main channel.

17. The system of claim 11, wherein the chamber includes a diaphragm disposed along the circumference of the piston such that the diaphragm seals the space between the piston and the chamber inner walls.

18. The system of claim 11 further comprising a motor connected to the piston to enable the reciprocating movement of the piston.

* * * * *